United States Patent
Gupta et al.

(10) Patent No.: US 7,614,279 B2
(45) Date of Patent: Nov. 10, 2009

(54) DETERMINATION OF PORE STRUCTURE CHARACTERISTICS OF FILTRATION CARTRIDGES AS A FUNCTION OF CARTRIDGE LENGTH

(75) Inventors: Krishna M. Gupta, Ithaca, NY (US); Akshaya Jena, Ithaca, NY (US)

(73) Assignee: Porous Materials, Inc., Ithaca, NY (US)

( * ) Notice: Subject to any disclaimer, the term of this patent is extended or adjusted under 35 U.S.C. 154(b) by 197 days.

(21) Appl. No.: 11/548,067

(22) Filed: Oct. 10, 2006

(65) Prior Publication Data
US 2008/0083266 A1    Apr. 10, 2008

(51) Int. Cl.
*G01N 15/08* (2006.01)
*B01D 39/00* (2006.01)

(52) U.S. Cl. .............................. 73/38; 210/85; 210/87; 210/90

(58) Field of Classification Search .............. 73/38; 210/85, 87, 90
See application file for complete search history.

(56) References Cited

U.S. PATENT DOCUMENTS

| | | | | |
|---|---|---|---|---|
| 4,069,704 A | * | 1/1978 | Grant et al. ............... | 73/38 |
| 4,223,551 A | * | 9/1980 | Greve et al. ............... | 73/38 |
| 4,332,679 A | * | 6/1982 | Hengst et al. ............. | 210/90 |
| 4,341,109 A | * | 7/1982 | Evans, Jr. ................. | 73/37 |
| 4,348,887 A | * | 9/1982 | Lorenz et al. ............. | 73/23.2 |
| 4,355,535 A | * | 10/1982 | Vaughan .................. | 73/37.8 |
| 4,471,650 A | * | 9/1984 | Koch ....................... | 73/38 |
| 4,495,795 A | | 1/1985 | Gupta | |
| 4,538,450 A | * | 9/1985 | Koch ....................... | 73/38 |
| 4,660,412 A | | 4/1987 | Gupta | |
| 5,428,987 A | * | 7/1995 | Rousseau ................. | 73/38 |
| 6,684,685 B2 | | 2/2004 | Gupta et al. | |
| 6,706,189 B2 | * | 3/2004 | Rabie et al. .............. | 210/636 |
| 6,766,257 B2 | | 7/2004 | Gupta et al. | |

(Continued)

OTHER PUBLICATIONS

Jena and Gupta, Pore Size Distribution in Porous Materials, Proceedings of International Conference Filtration 99, Nov. 3-4, Chicago, INDA, 1999.
Jena and Gupta, Characterization of Pore Structure of Filtration Media, Fluid/Particle Separation Journal, vol. 14, No. 3, 2002, pp. 227-241.

(Continued)

*Primary Examiner*—David A. Rogers
(74) *Attorney, Agent, or Firm*—Thomas T. Aquilla

(57) ABSTRACT

A method for determining pore structure characteristics of a filtration cartridge includes the steps of placing a porometry test location isolating device in sealing contact with the filtration cartridge at a desired test location, increasing the porometer test gas pressure until the test gas flows through the cartridge at the test location, measuring the flow rate of the test gas through the test location as a function of differential pressure, reducing the test gas pressure to atmospheric pressure, wetting the test location with a wetting liquid, increasing the test gas pressure again until the test gas flows through the cartridge at the test location, measuring differential gas pressure and gas flow rates through the test location, and converting the measured gas flow rates and differential pressures into through pore throat diameters, largest through pore throat diameter, mean flow through pore throat diameter, pore distribution, and gas permeability of the cartridge.

14 Claims, 6 Drawing Sheets

U.S. PATENT DOCUMENTS

| | | |
|---|---|---|
| 6,789,410 B1 | 9/2004 | Gupta et al. |
| 6,845,651 B2 | 1/2005 | Gupta et al. |
| 7,040,141 B2 | 5/2006 | Gupta et al. |
| 2002/0036163 A1* | 3/2002 | Miller et al. ............... 210/248 |
| 2002/0189988 A1* | 12/2002 | Alexander et al. .......... 210/169 |
| 2005/0115879 A1* | 6/2005 | Kochergin et al. .......... 210/193 |
| 2007/0001324 A1* | 1/2007 | Cote et al. ............... 261/122.1 |
| 2007/0221584 A1* | 9/2007 | Ruprecht .................... 210/767 |

OTHER PUBLICATIONS

Jena and Gupta, Liquid Extrusion Techniques for Pore Structure Evaluation of Nonwovens, International Nonwovens Journal, vol. 12, No. 3. 2003, pp. 45-53.

Jena and Gupta, Pore Structure Characteristics and Gas Permeability of Complete Filter Cartridges, Filtech 2005, p. II-218.

* cited by examiner

PRIOR ART

CARTRIDGE

DETERMINATION OF PORE STRUCTURE CHARACTERISTICS OF FILTRATION CARTRIDGES AS A FUNCTION OF CARTRIDGE LENGTH

BACKGROUND OF THE INVENTION

1. Field of the Invention

The invention pertains to the field of flow porometry. More particularly, the invention pertains to a method and apparatus for the use of flow porometry to determine the pore structure characteristics of filtration cartridges as a function of the cartridge length.

2. Description of Related Art

Filtration cartridges are workhorses of modern industry. Filtration cartridges essentially are used for the separation of suspended solids from liquids and/or gases. Numerous applications of filtration cartridges are found in a wide range of industries, including biotechnology, chemical, pharmaceutical, food and drink, medical, electronic, automobile, and the construction industries. A wide variety of tasks are performed by filtration cartridges, such as, for example, filtration of bacteria, pollen and cells from bodily fluids, purification of chemicals, detoxification of waste water, removal of heavy ions from water for use in the electronic industry, purification of pharmaceutical products, removal of pathogens and solids from soft drinks, and removal of excess water from slurries.

The performance of the filtration media and the ability to separate solids from fluids are determined by the pore structure characteristics of the filtration media. Relevant pore structure characteristics of filtration media include, for example, through pore throat diameters, the largest through pore throat diameter, mean flow through pore throat diameter, pore distribution, and fluid permeability.

For purposes of product development and/or quality control, for example, it is often desirable to measure such pore structure characteristics of filtration cartridges. Such pore structure characteristics of filtration media generally can be accurately measured in a flow porometer, such as the Capillary Flow Porometer of Porous Materials, Inc. (See Akshaya Jena and Krishna Gupta, *Characterization of Pore Structure of Filtration Media*, Fluid/Particle Separation Journal, Vol. 14, No. 3, 2002, pp. 227-241, and Akshaya Jena and Krishna Gupta, *Liquid Extrusion Techniques for Pore Structure Evaluation of Nonwovens*, International Nonwovens Journal, Vol. 12, No. 3. 2003, pp. 45-53, the complete disclosures of which are hereby incorporated herein by reference in their entireties). Porous Materials, Inc. is a pioneer in the field of flow porometry and has obtained several patents in the field, including U.S. Pat. No. 6,766,257, which describes PMI Capillary Flow Porometry, and U.S. Pat. No. 6,684,685, the complete disclosures of which are hereby incorporated herein by reference in their entireties.

U.S. Pat. No. 6,684,685 discloses a liquid extrusion porosimeter and method for evaluating porosity characteristics (specifically, pore volume, pore distribution and liquid permeability) of porous materials, such as filtration media. The porosimeter includes a fluid reservoir located below the sample, and a penetrometer comprising a vessel that catches any fluid displaced from the reservoir of fluid, wherein a level of fluid rises in the penetrometer when additional fluid enters the penetrometer. The sample is preferably wetted, with the same type of fluid that is in the reservoir, prior to placing the sample on the porosimeter. The porosimeter preferably also includes a membrane located between the sample and the reservoir of fluid. The membrane has pores with a size smaller than any of the sample pores. Pore volume of the sample is determined by measuring the change in fluid level in the penetrometer after pressure, which is above the bubble point pressure of the sample but below the bubble point pressure of the membrane, is applied to the sample. Permeability is measured by measuring rate of flow while the liquid level is above the sample.

The PMI Capillary Flow Porometer is a completely automated instrument. It measures pressures of the test gas accurately. It increases pressure in small increments, allows the system to equilibrate, and then records the increase in pressure. The flow rate through the sample is also measured accurately. Pressures can be raised to high values or reduced from high values to very low values. The porometer delivers the compressed gas through a tube to the sample chamber, which can be designed to hold samples of various sizes and shapes.

The technique of flow porometry is based on the simple principle that a wetting liquid spontaneously fills the pores of filtration media. For the wetting liquid, the surface free energy of the filtration media with the liquid is less than the surface free energy of the filtration media with air. Therefore, filling of the pores by the wetting liquid is accompanied by a decrease in free energy and the filling process is spontaneous. The wetting liquid cannot spontaneously flow out of the pores, however, it can be removed from the pores by a pressurized non-reacting gas.

The gas pressure needed to displace a wetting liquid from a pore is related to the pore diameter, as follows:

$$p = 4\gamma \cos\theta / D \quad (1)$$

where, p is the differential gas pressure on the wetting liquid in the pore, $\gamma$ is the surface tension of the wetting liquid, $\theta$ is the contact angle of the wetting liquid with the filtration media, and D is the pore diameter. The test involves measurement of gas flow rates through a dry sample as a function of differential pressure. The differential pressure is reduced to zero, the sample is wetted with a wetting liquid, and gas flow rates through the wet sample are measured as a function of differential pressure. FIG. 1 shows a schematic plot of gas flow rates through a sample in dry and wet conditions, and FIG. 2 shows a graph of pore size distribution.

The wet curve generated by the wet sample shows no gas flow with increase in differential pressure at the beginning of the test, because all of the pores are filled with the wetting liquid. The first pore to be emptied at the lowest pressure is the largest pore (see Equation 1 above). The differential pressure that initiates gas flow through a wet sample yields the largest through pore diameter (FIG. 1).

The diameter of a pore can change along the pore path. The differential gas pressure that is sufficient to displace liquid from the pore throat can completely empty the pore and initiate gas flow. Therefore, the pore diameter computed from the measured differential pressure yields the through pore throat diameter. The measured largest pore diameter is the largest through pore throat diameter. The dry curve is produced by the dry sample. The half-dry curve represents computed data that yield half of the gas flow rate through the dry sample at a given differential pressure. The differential pressure at which the wet curve and the half-dry curve have the same flow rates yields the mean flow through pore throat diameter. The mean flow pore diameter is such that half of the flow is through pores smaller than the mean flow pore and the rest of the flow is through pores larger than the mean flow pore. The ratio of flow rates through the wet sample and the dry sample also yields flow distribution over pore diameter (FIGS. 1 and 2). This distribution has been shown to be close to pore fraction distribution (See A. K. Jena and K. M. Gupta, *Pore Size Distribution in Porous Materials*, Proceedings of International Conference Filtration 99, November 3-4, Chicago, INDA, 1999). Gas permeability is computed from measured gas flow rates through the dry sample using Darcy's law (See P. C. Carman, *Flow of Gases through Porous Media*, Academic Press, 1956).

Characteristics of filtration media that can be measured accurately by flow porometry include, for example, the constricted pore diameter, the largest pore diameter, the mean flow pore diameter, pore distribution, gas permeability, liquid permeability, envelope surface area and effects of operational variables, such as temperature, pressure, chemical environment and stress. Demonstrated applications of flow porometry include analysis of pore characteristics in the thickness direction, pore characteristics in the x-y plane, properties of individual layers of multi-layered products determined in-situ without separating the layers, and evaluation of properties without cutting samples and damaging the products. See, e.g., U.S. Pat. Nos. 6,766,257, 6,789,410, 6,845,651, and 7,040,141.

U.S. Pat. No. 6,766,257 discloses a method of determining the pore structure of the individual layers in a multi-layered composite porous material, including the steps of providing a sample of a multi-layered porous material, sealing the sample in suitable test chamber, filling the pores of the sample material with a wetting liquid, such that the liquid/sample surface free energy is less than the gas/sample surface free energy, using a non-reacting gas to apply pressure to one side of the sample sealed in the test chamber, increasing the gas pressure gradually, so as to displace the liquid from the pores, increasing gas flow through the sample, measuring the pressure at which liquid flows from each successive layer of the sample material, and calculating the pore structure using an equation selected from the group consisting of $p=\gamma(dS/dV)$, $D=4\gamma/p$, and $f=-d[100(F_w/F_d)]/dD$.

U.S. Pat. No. 6,789,410 discloses a porosimeter that includes a pressurizable sample chamber with a membrane located directly below the sample. The membrane pores have a smaller size than any of the sample pores of interest. A fluid reservoir is located below the membrane such that the reservoir and the membrane form a seal. In operation, as fluid enters the fluid reservoir through the membrane or a reservoir inlet, fluid already in the fluid reservoir is displaced through a reservoir exit. An inlet in a fluid displacement reservoir receives the fluid displaced from the fluid reservoir. A recirculation line receives fluid from the exit of the fluid displacement reservoir and circulates the fluid into the inlet of the fluid reservoir. In a preferred embodiment, a pump recirculates the fluid through the recirculation line. Fluid returned to the reservoir circulates over the bottom of the membrane, and sweeps air bubbles out of the reservoir.

U.S. Pat. No. 6,845,651 discloses a method and apparatus for determining surface area and pore distribution of a sample. A pressurizable sample chamber of known volume holds a sample with unknown porosity characteristics. The sample chamber has a known pressure (or vacuum). A flow controller preferably controls the flow of the pure gas to be adsorbed by the sample in the sample chamber. A pressure monitor preferably monitors the pressure in the sample chamber. Once the pressure approaches a target pressure, the flow controller is closed. The pressure monitor continues to monitor the pressure until it stops changing when an equilibrium is attained. The amount of gas introduced into the system through the flow controller and the volume and final pressure of the sample chamber are used to calculate the amount of gas adsorbed. This calculation is subsequently used to determine the porosity characteristics of the sample. Some of these characteristics include, but are not limited to, pore distribution and surface area.

U.S. Pat. No. 7,040,141 discloses a method and apparatus for determining porosity characteristics of a sample having a plurality of pores, located within a pressurizable chamber. The sample divides the chamber into a first volume and a second volume. A known amount of vapor is introduced into the first volume and the second volume at the same pressure ($P_x$). After equilibrium is reached, pressure and decrease in volume of vapor are measured. Pore diameter and pore volume are calculated. A pressure differential is created between the two volumes, and the pressure change is monitored after the pressure differential is introduced. In a preferred embodiment, the pressure is increased in the first volume by a small percentage ($\Delta P_x$), and the pressure change on both sides of the sample is monitored after the pressure increase. The flow rate of the vapor is calculated using the pressure change. These steps are preferably repeated. The pore distribution in the sample is preferably calculated from the flow rates.

Although there are known methods and apparatus that are intended to aid in the analysis of pore structure characteristics of filtration media, one problem with the known methods is that they are not well-suited for analyzing the pore structure characteristics of filtration cartridges as a function of cartridge length. Thus, the known methods do not allow the pore structure of a filtration cartridge to be determined at a selected location along the length of the cartridge, and do not allow the pore structure of the cartridge to be evaluated as a function of cartridge length.

Thus, there is a need in the art for a method and apparatus for using flow porometry to determine the pore structure characteristics of filtration cartridges as a function of cartridge length.

SUMMARY OF THE INVENTION

The present invention provides methods and apparatus for using flow porometry to determine the pore structure characteristics of filtration cartridges as a function of cartridge length. The apparatus according to the invention provides several porometry test location isolating devices designed for using a flow porometer to determine the pore structure characteristics at any location along the length of a filtration cartridge, including means for directing the flow of a pressurized test gas through a preselected test location along the length of the filtration cartridge. The test location isolating devices easily are operatively connected to a porometer to enhance its ability to determine pore structure characteristics of a cartridge as a function of its length. Various alternative embodiments include test location isolating devices provided as inserts, rings, and sleeves that slidingly engage either the inner or outer surface of the filtration cartridge and direct the test gas through the selected test location along the length of the cartridge.

Briefly stated, a method according to the invention provides for determining the pore structure characteristics of a filtration cartridge, including the steps of placing a porometry test location isolating device in sealing contact with the filtration cartridge at a desired test location, increasing the porometer test gas pressure until the test gas flows through the cartridge at the test location, measuring the flow rate of the test gas through the test location as a function of differential pressure, reducing the test gas pressure to atmospheric pressure, wetting the test location with a wetting liquid, increasing the test gas pressure again until the test gas flows through the cartridge at the test location, measuring differential gas pressure and gas flow rates through the test location, and converting the measured gas flow rates and differential pressures into through pore throat diameters, largest through pore throat diameter, mean flow through pore throat diameter, pore distribution, and gas permeability of the cartridge.

In the preferred embodiment, the invention provides a porometry test location isolating device comprising an insert adapted to slidingly engage the inner surface of the inner cylindrical bore of a filtration cartridge. The apparatus includes a tubular member having a test gas inlet at its first end and a sealed second end, a plurality of radial gas channels arranged between the first and second ends of the tubular member for directing flow of the pressurized test gas through the tubular member to the test location of the cartridge, and a pair of O-rings seated within a pair of circumferential O-ring grooves arranged between the radial gas channels and the first and second ends of the tubular member, the O-rings defining the test location and confining flow of the pressurized test gas through the test location.

In an alternative embodiment, the invention provides a porometry test location isolating device comprising an insert adapted to slidingly engage the inner surface of the cylindrical bore of a filtration cartridge. The apparatus includes a tubular member having a test gas inlet at its first end and a sealed second end, a plurality of radial gas channels arranged between the first and second ends of the tubular member for directing flow of the pressurized test gas through the tubular member to the test location of the cartridge, and a pair of gaskets seated within a pair of circumferential gasket grooves arranged between the radial gas channels and the first and second ends of the tubular member, the gaskets defining the test location and confining flow of the pressurized test gas through the test location, and a pair of flexible members attached to the ends of the tubular member for pulling the insert through a filtration cartridge having an irregular shape or a bent or deformed cartridge.

In yet another alternative embodiment, the invention provides a porometry test location isolating device comprising a ring adapted to slidingly engage an outer surface of a cylindrical filtration cartridge. The apparatus includes a ring member having a groove within an inner surface thereof defining a central gas channel connected to a test gas inlet, the central gas channel being arranged to direct the flow of the test gas through the ring member to the test location of the cartridge, and a pair of gaskets seated within a pair of gasket grooves arranged on each side of the central gas channel, the gaskets defining the test location and confining flow of the pressurized test gas through the test location.

In still yet another alternative embodiment, the invention provides a porometry test location isolating device comprising a pair of sleeves adapted to slidingly engage an outer surface of a cylindrical filtration cartridge. The apparatus includes a pair of tight fitting rubber sleeves slidingly engaged at each end of a filtration cartridge, the gap between the rubber sleeves defining the test location and confining flow of the pressurized test gas through the test location, and a test gas inlet located at an end of one of the sleeves, and a sealed end located at an end of the other of the sleeves, with the cartridge being arranged between the sleeves.

The invention provides the advantage of enabling the analysis of the pore structure characteristics of filtration cartridges as a function of cartridge length. Thus, the invention allows the pore structure of a filtration cartridge to be determined by flow porometry at any location along the length of the cartridge, and allows the pore structure characteristics of the cartridge to be evaluated as a function of cartridge length. Furthermore, the invention provides means for employing a quick scan along the length of a cartridge as an aid in identifying the presence of major defects.

These and other features and advantages will become readily apparent from the following detailed description, which should be read in conjunction with the accompanying drawing figures.

BRIEF DESCRIPTION OF THE DRAWINGS

The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF THE INVENTION

Figure 1:
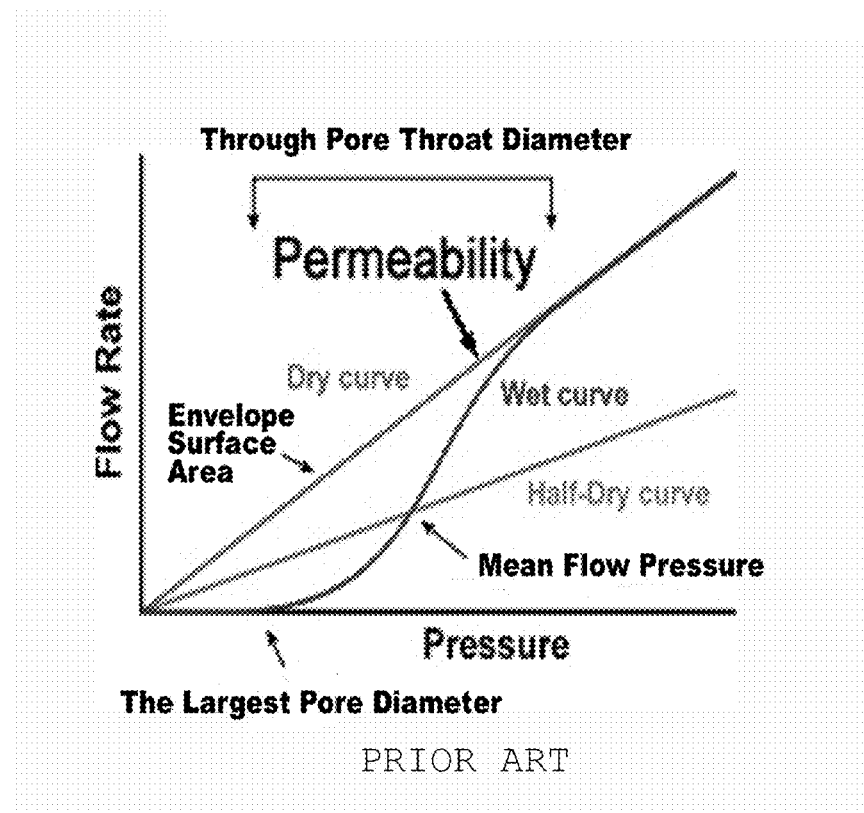
FIG. 1 shows a graph depicting various pore structure characteristics measurable by flow porometry.
Figure 2:
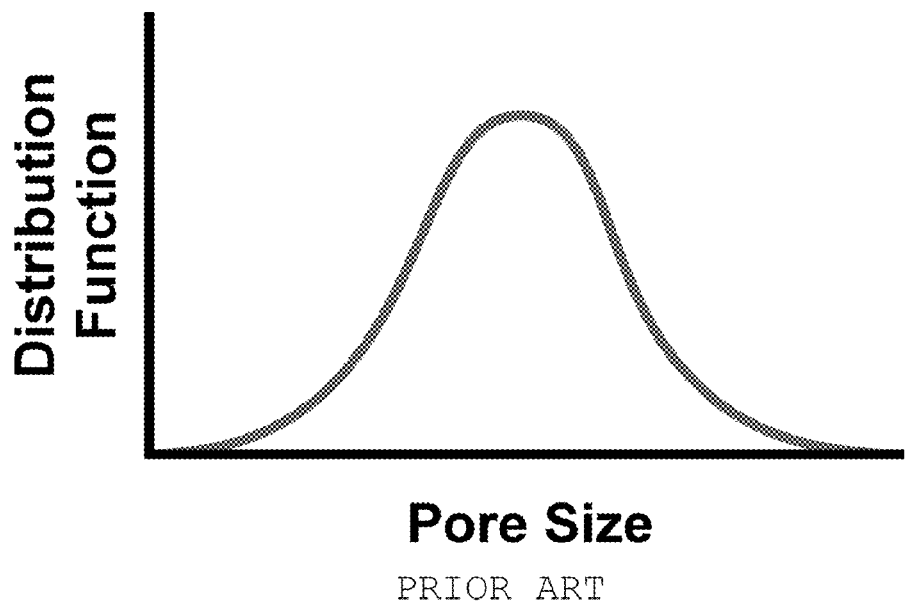
FIG. 2 shows a graph depicting pore size distribution.

The following description relates to certain preferred embodiments of apparatus and methods for using flow porometry to determine the pore structure characteristics of filtration cartridges as a function of cartridge length. It will be readily apparent that numerous variations and modifications other than those specifically indicated will be readily apparent to those of sufficient skill in the art. In addition, certain terms are used throughout the discussion in order to provide a convenient frame of reference with regard to the accompanying drawings, such as "inside", "outside", and the like. Such terms are not intended to be specifically limiting of the invention, except where so indicated in the claims.

Filtration cartridge product development ideally requires measurement of pore structure characteristics of complete filtration cartridges for design and performance evaluation. Important pore structure characteristics required for filtration cartridges include through-pore throat diameters, the bubble point pore diameter, mean flow pore diameter, and pore distribution. All of these characteristics can be measured by capillary flow porometry. However, testing of a complete filter cartridge by capillary flow porometry is a major challenge, because of the high gas flow rates through large cartridges, large size of the sample holder, need for accurate measurement of pressure drop, and requirement of sufficient supply of gas for a reasonable time.

The pore structure characteristic of an entire filter cartridge can be measured by a porometer, provided that the porometer is capable of accommodating the complete cartridge in the sample chamber, producing very high flow rates of gas for large cartridges, accurately measuring flow rates and pressure drops in such a system, and supplying adequate amount of gas for the test duration. The PMI Complete Filter Cartridge Analyzer has all of these features and we have recently shown that it is capable of measuring the relevant pore structure characteristics of an entire filtration cartridge (Akshaya Jena and Krishna Gupta, *Pore Structure Characteristics and Gas Permeability of Complete Filter Cartridges*, Proceedings, Filtech, Germany, Oct. 11-13, 2005).

Limitations of Available Techniques: Filter cartridges are often long, so that their output is high. The pore structure of a long cartridge normally is not uniform. Large size pores, increased or decreased concentration of pores, and defects produced during manufacturing due to factors such as non-uniform distribution of powders or fibers, non-uniform compaction, and improper sintering or hot pressing may be present at a number of locations along the length of a long cartridge. However, the presence of such structural abnormality is not usually revealed, when the entire cartridge is tested as a whole. Thus, the performance of a cartridge may be poor, even though the overall pore structure of the entire cartridge containing defects along its length appears to be satisfactory. It is, therefore, imperative to be able to measure the pore structure characteristics of a complete filtration cartridge at various locations along its length, to eliminate cartridges with unacceptable defects, and/or make changes in processing techniques used for the manufacture of the cartridges, so as to avoid or minimize such defects. However, due to the foregoing problems, currently available methods do not allow for the measurement of the pore structure characteristics of a complete filtration cartridge at various locations along its length.

In the present invention, we disclose novel apparatus and methods that have been developed to determine the pore structure at various locations along the length of a filtration cartridge, using a flow porometer (i.e., the PMI Capillary Flow Porometer). The methods and apparatus disclosed herein have been successfully used to measure various relevant characteristics of through pores, including throat diameters, largest throat diameter, mean flow pore throat diameter, pore distribution, and permeability.

Figure 3:
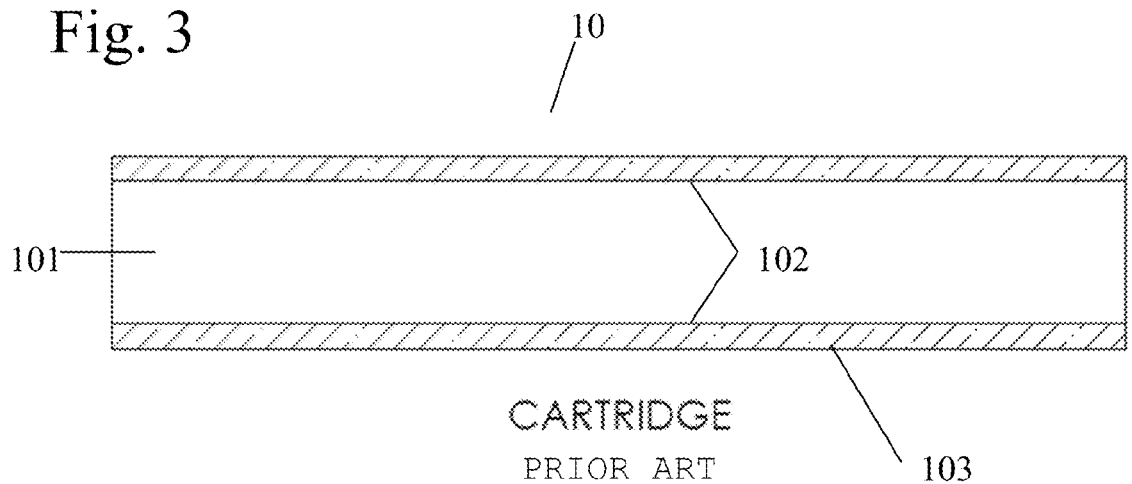
FIG. 3 shows a transverse sectional view of a typical filtration cartridge that can be analyzed by flow porometry in accordance with the present invention.

Equipment: The typical filtration cartridge (FIG. 3) is a hollow cylindrical shape with a porous wall and a cross-section that normally is circular. Fluids (liquid or gas) pass through the pores, while solid particles in the fluid are held back by the pores. The fluid moves either from the inside to the outside or from the outside to the inside.

In order to test a selected location on the cartridge, we devised methods and specialized apparatus to permit flow of the test gas only through a selected test location of the filter. These techniques generally involve the use of specially designed test location isolating devices, such as inserts, rings, or sleeves that slide either inside or outside the cartridge, several examples of which are described below.

Figure 4:
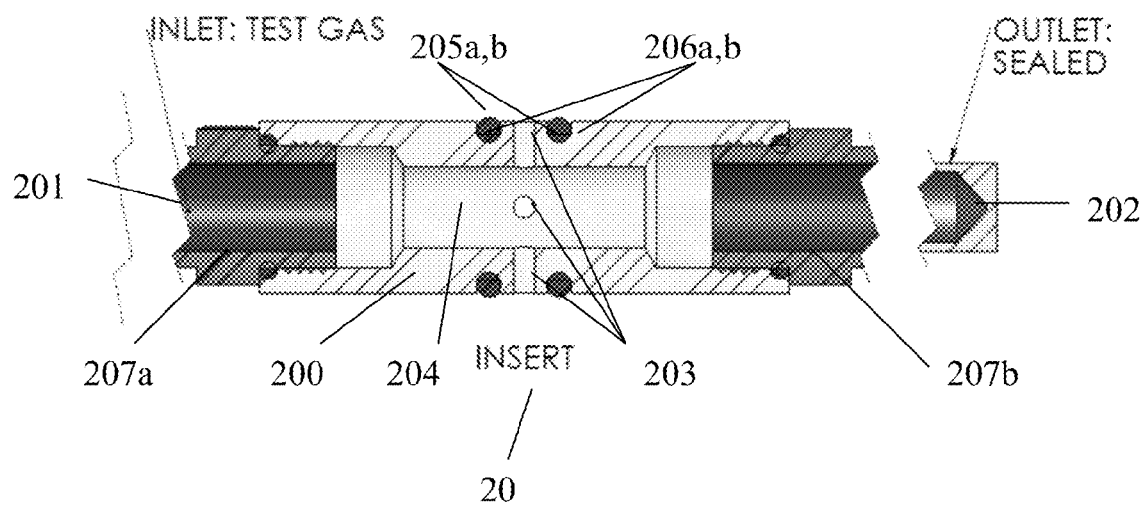
FIG. 4 shows a sectional view of a porometry test location isolating device, according to an embodiment of the present invention, specially adapted to slide inside the cylindrical bore of a filtration cartridge.

Referring now to FIG. 4, a porometry test location isolating device 20 according to an embodiment of the present invention is shown, specially adapted to slide inside the cylindrical bore 101 of a filtration cartridge 10. The test location isolating insert 20 comprises a tubular member 200 having a test gas inlet 201 at its first end and a sealed second end 202. In roughly the central region of the length of the insert, a plurality of radial gas channels 203 is arranged between the first and second ends 201, 202 of the tubular member 200, extending from the inner central bore 204 of the insert to the outside of the insert for directing flow of the pressurized test gas through the tubular member to the test location of the cartridge. FIG. 4 shows three radial gas channels (the fourth being obscured in the drawing), however, the number can vary. Two O-rings 205a, 205b are seated within the two circumferential O-ring grooves 206a, 206b on each side of the radial gas channels 203. The O-rings 205a, 205b effectively define the test location by confining the flow of the pressurized test gas through the area between the O-rings. A pair of end tubes 207 is threaded to the ends 201, 202 of the tubular member 200 to make airtight O-ring seals with the tubular member. Compressed test gas is introduced through the test gas inlet 201 and into the central bore 204, preferably via one of the end tubes 207a. The free end of the other tube 207b is sealed to prevent escape of the test gas.

The tube with sealed end 207b is pushed inside the cartridge 10 until the desired test location is within the two circumferential O-rings 205a, 205b on the tubular member 200. The O-rings 205a, 205b are such that air-tight seals are made between the tubular member 200 and the inner surface 102 of the cartridge 10, and that the insert 20 can be pushed from one end of the cartridge to the other for taking measurements at a particular location or taking multiple measurements along the length of the cartridge.

Figure 5:
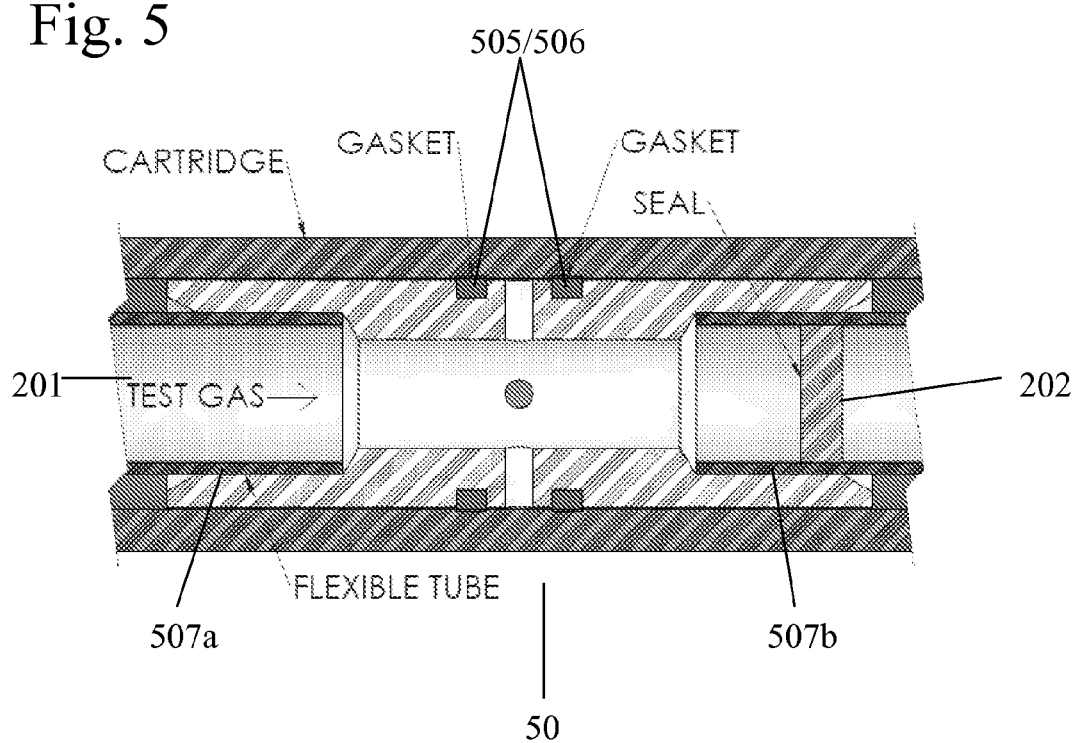
FIG. 5 shows a porometry test location isolating device, according to an alternative embodiment of the present invention, specially adapted for being pulled inside a filtration cartridge.

Different inserts can be designed, depending upon the shape or configuration of the filtration cartridge being tested, such that the inserts match the shape of the cartridge. FIG. 5 shows an alternative embodiment of an insert similar to that of FIG. 4, but which is attached to flexible end tubes 507a, 507b and employs gaskets 505a, 505b, instead of O-rings, within grooves 506a, 506b. This insert is designed to be more flexible, so that it can be pulled inside a bent cartridge (or a cartridge of unusual configuration) to the desired location for determination of the pore structure at a particular location or as a function of cartridge length.

Figure 6:
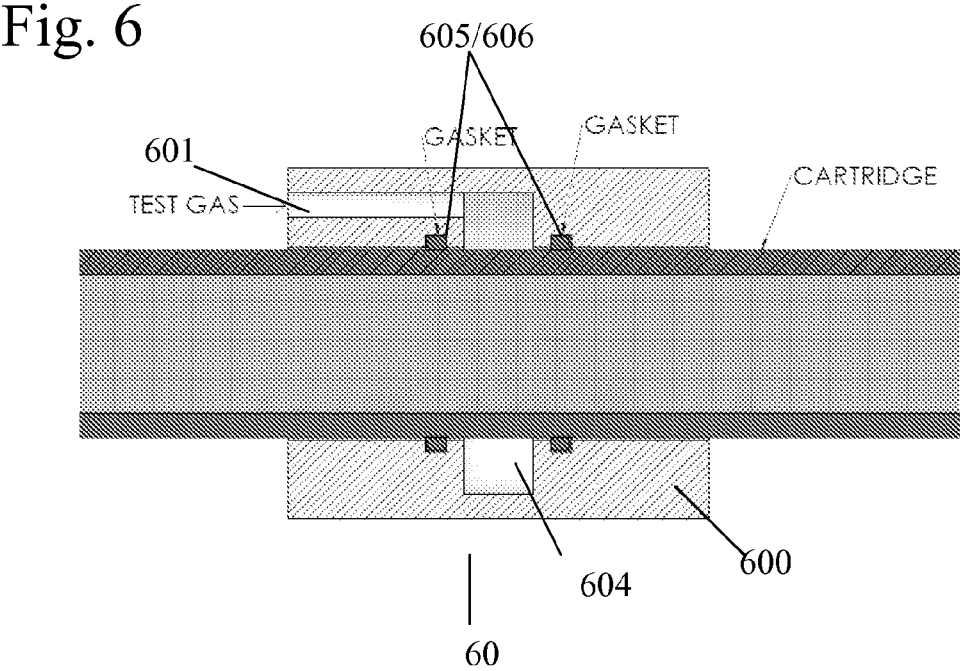
FIG. 6 shows a porometry test location isolating device, according to another alternative embodiment of the present invention, comprising a ring member specially adapted for sliding over the outside surface of a filtration cartridge.

Referring now to FIG. 6, yet another alternative embodiment of a test location isolating device according to the invention is shown, specially adapted to slide over the outside of a filtration cartridge. The test location isolating ring 60 comprises a ring member 600 having a groove around an inner surface thereof defining a central gas channel 604 arranged to direct the flow of the test gas through the ring member to the test location of the cartridge. The central gas channel 604 is connected to a test gas inlet 601. A pair of gaskets 605a, 605b is seated within a pair of gasket grooves 606a, 606b arranged on each side of the central gas channel 604. The gaskets 605a, 605b effectively define the test location by confining the flow of the pressurized test gas through the area between the gaskets. Rings of various sizes can be designed to slide over the outside surface of the cartridge, and the desired test location on the cartridge can be brought inside the ring for testing by sliding the cartridge inside the ring.

Figure 7:
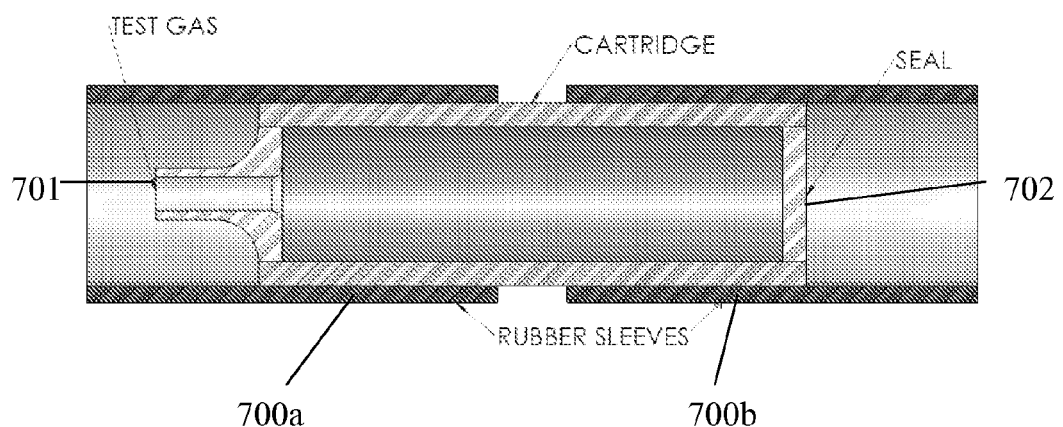
FIG. 7 shows a porometry test location isolating device, according to another alternative embodiment of the present invention, comprising a pair of sleeves specially adapted for sliding over the outside surface of a filtration cartridge

FIG. 7 shows still yet another alternative embodiment of a test location isolating device according to the invention, specially adapted to slide over the outside of a filtration cartridge. In this embodiment, the filtration cartridge 10 is inserted inside two tight fitting rubber sleeves 700a, 700b slidingly engaged over the ends of the cartridge. The gap between the rubber sleeves defines the test location by confining the flow of the pressurized test gas through the area between the sleeves. A test gas inlet 701 is located at an end of one of the sleeves, and a sealed end 702 is located at an end of the other of the sleeves, with the cartridge being arranged between the sleeves. Because the test area is exposed between the sleeves, this variation is particularly suitable for cartridges having irregular cross-sections.

Test Procedure: The porometer is connected to the assembly of cartridge and the test location isolating device, such as insert or ring or sleeve. The test location isolating device is moved either manually or automatically by the porometer to the desired location. The porometer increases the pressure of the test gas in small increments. The gas is constrained to flow through the pores in the wall of the cartridge at the desired location. Gas flow rate through the selected part of the cartridge is measured as a function of differential pressure. The gas pressure is then reduced to atmospheric pressure, the test area is wetted with a wetting liquid, and gas pressure is slowly increased. Differential gas pressure and gas flow rates through the wet location are measured. The measured gas flow rates and differential pressures are converted into through pore throat diameters, the largest through pore throat diameter, mean flow through pore throat diameter, pore distribution, and gas permeability of the selected annular location on the cartridge wall. Pore structure characteristics at different locations are determined by moving the test location isolating device to the desired location. The pore structure characteristics of the cartridge as a function of its length can be determined by performing tests at locations with increasing length. Any sudden variation in the pore structure may be obtained by measuring flow rate as a function of length.

Figure 8:
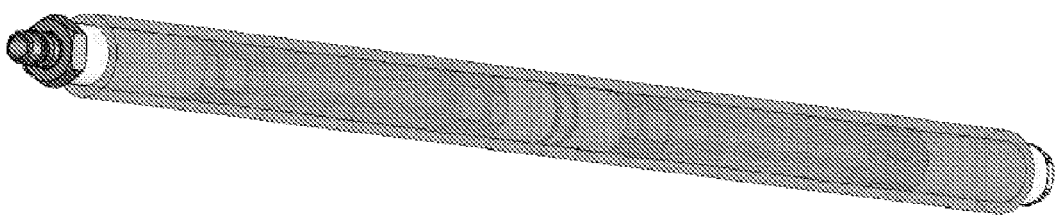
FIG. 8 shows a porometry test location isolating device, according to yet another alternative embodiment of the present invention, specially adapted to slide inside the cylindrical bore of a filtration cartridge.

Example of Successful Application of the Invention: The invention was used to determine the pore structure characteristics of a long cartridge at different locations along its length. It had a wall thickness of about 3/16th inch. For this particular application, an insert made out of Teflon was used. The holes in the insert were about 1/8th inch in diameter and four in number. The circumferential o-rings were about 7/16th inch apart. The stainless steel tubes attached to the insert were long enough for the insert to be placed any where along the length of the cartridge. The arrangement is shown in FIG. 8. The loosely fitting plugs attached to the tubes extending from the insert at the two ends were for keeping the device straight and reducing any stress on the cartridge.

Figure 9:
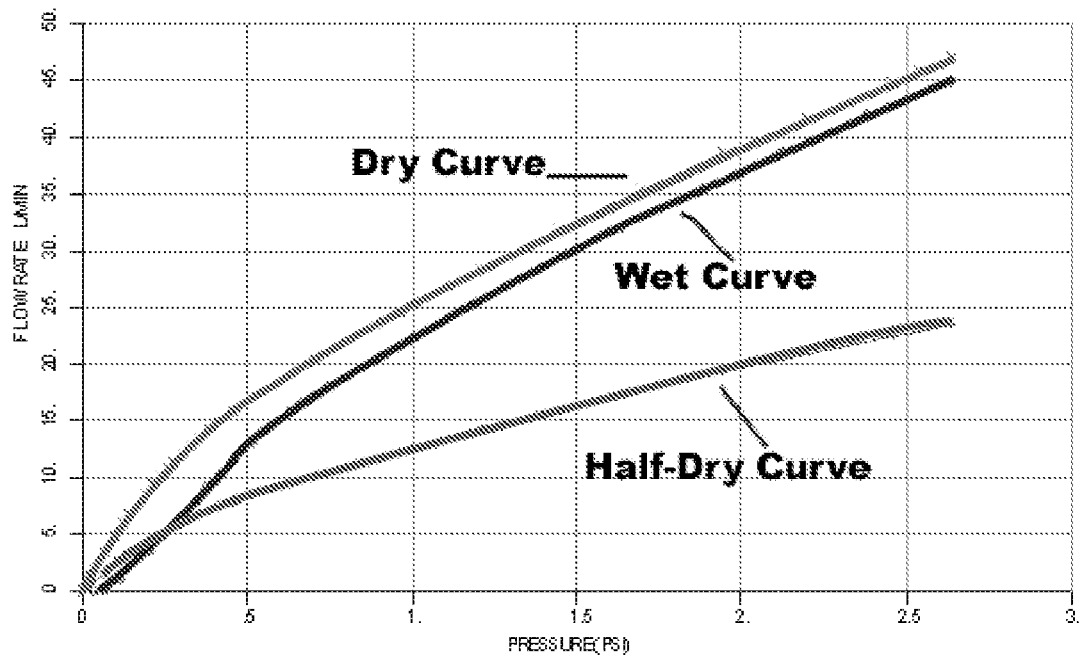
FIG. 9 shows a graph depicting porometry gas flow rates measured as functions of differential pressure through a portion of a filtration cartridge at the center of its length, in accordance with the present invention

The fully automated PMI Capillary Flow Porometer was used to supply compressed gas to the insert through the stainless steel tube and acquire the required data. The wetting liquid Galwick® (Propene,1,1,2,3,3,3-hexafluro oxidized, polymerized) was used to wet the cartridge. The measured flow rates through the part of the cartridge at its center in dry and wet conditions are shown in FIG. 9 as dry curve and wet curve respectively. The half-dry curve in the figure is computed to yield half of the flow rate through the dry sample at the same differential pressure.

Figure 10:
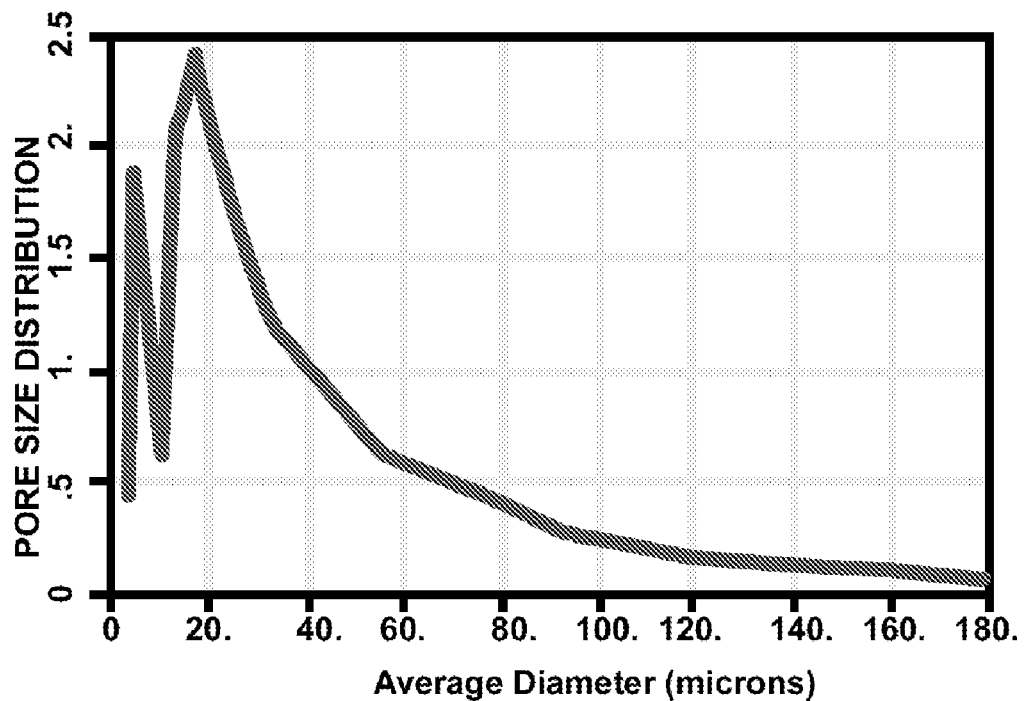
FIG. 10 shows a graph depicting pore distribution in the center of the length of the filtration cartridge of FIG. 9, in accordance with the present invention.

Using these experimental data and using the procedure described above, the porometer computed the largest through pore throat diameter and the mean flow through pore throat diameter as 227.6 μm and 30.62 μm respectively in the center of the length of the cartridge. The pore distribution is given in terms of the distribution function, f, as follows:

$$f = -[d(F_w/F_d) \times 100]/dD \qquad (2)$$

where $F_w$ and $F_d$ are gas flow through wet and dry samples respectively. The distribution curve is shown in FIG. 10. The distribution function is such that area under the function in any pore size range yields percentage gas flow through pores in that range. The pore distribution is close to the pore number distribution.

Dry curve gave the gas flow rates through the dry sample. These flow rates were utilized to compute gas permeability of the sample using Darcy's law.

Figure 11:
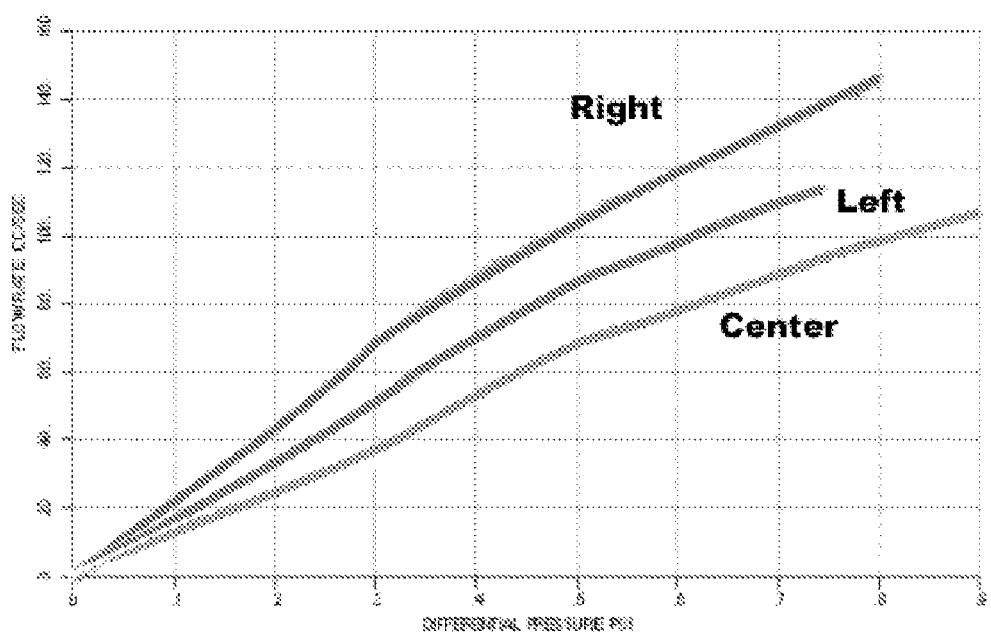
FIG. 11 shows a graph depicting gas flow rates through the center and the two ends of a long filtration cartridge, in accordance with the present invention.

Thus, all of the important pore structure characteristics at the center of the length of the cartridge were measured. By sliding the insert inside the cartridge, pore structures in other locations also were measured. Pore structures in this cartridge changed appreciably with length of the cartridge. For example, the mean flow through pore throat diameters at the two ends of the cartridge were 5.9% and 12.5% lower than the mean flow through pore throat diameter in the center. The variation in the gas flow rates at the two ends and at the center of a cartridge are shown in FIG. 11.

The present invention thus provides the advantage of enabling the analysis of the pore structure characteristics of filtration cartridges as a function of cartridge length. The invention allows the pore structure of a filtration cartridge to be determined by flow porometry at any location along the length of the cartridge, and allows the pore structure characteristics of the cartridge to be evaluated as a function of cartridge length. Furthermore, the invention provides means for employing a quick scan along the length of a cartridge as an aid in identifying the presence of major defects, and has numerous applications in the development and manufacture of filtration cartridges.

It is to be understood that the architectural and operational embodiments described herein are exemplary of a plurality of possible arrangements to provide the same (or equivalent) general features, characteristics, and general system operation. Therefore, while there have been described the currently preferred embodiments of the present invention, those skilled in the art will recognize that other and further modifications may be made, without departing from the spirit of the present invention, and it is intended to claim all modifications and variations as fall within the scope of the appended claims.

Accordingly, it must further be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. Test apparatus for using a flow porometer to determine pore structure characteristics of at least a portion of a filtration cartridge, comprising a porometry test location isolating device having means for directing flow of a pressurized test gas through only a preselected test location along the length of said filtration cartridge, means for applying pressure in small increments to said test location, means for measuring differential pressures of said test gas, and means for measuring a rate of flow of said test gas through said test location, wherein said test location isolating device is selected from the group consisting of inserts, rings, and sleeves that slidingly engage either an inner or outer surface of said filtration cartridge and direct said test gas through said test location of said cartridge, and wherein said test location isolating device comprises an insert adapted to slidingly engage an inner surface of a cylindrical bore of said filtration cartridge, said insert comprising:

a) a tubular member having a test gas inlet at a first end thereof and a sealed second end;

b) a plurality of radial gas channels arranged between said first and second ends of said tubular member for directing flow of said pressurized test gas through said tubular member to said preselected test location of said cartridge; and c) a pair of O-rings seated within a pair of circumferential O-ring grooves arranged between said radial gas channels and said first and second ends of said tubular member, said O-rings defining said test location and confining flow of said pressurized test gas through said test location.

2. The apparatus of claim 1, further comprising at least one solid member attached to one of said ends of said tubular member for pushing or pulling said insert through a filtration cartridge.

3. The apparatus of claim 1, operatively connected to a flow porometer and/or means for manually or automatically moving said test location isolating device along the length of said filtration cartridge.

4. A method for using a flow porometer to determine pore structure characteristics of at least a portion of a filtration cartridge, comprising the steps of:

a) providing a flow porometer and a filtration cartridge for analysis;

b) placing a porometry test location isolating device of claim 1 in sealing contact with said filtration cartridge at a preselected test location of said cartridge;

c) increasing a test gas pressure of said porometer incrementally, such that said test gas is constrained to flow through said filtration cartridge at said test location;

d) measuring a flow rate of said test gas through said test location as a function of differential pressure;

e) reducing said test gas pressure to atmospheric pressure;

f) wetting said test location with a wetting liquid;

g) increasing said test gas pressure again incrementally, such that said wetting liquid is constrained to flow through said filtration cartridge at said test location;

h) measuring differential gas pressure and gas flow rates through said test location; and i) converting said measured gas flow rates and differential pressures into through pore throat diameters, the largest through pore throat diameter, mean flow through pore throat diameter, pore distribution, and gas permeability of said filtration cartridge at said test location.

5. The method of claim 4, further comprising the step of determining pore structure characteristics of said filtration cartridge as a function of its length by performing tests at locations with increasing length.

6. The method of claim 4, further comprising the step of determining variation in pore structure by measuring flow rate as a function of length.

7. The method of claim 4, comprising the step of determining said pore structure characteristics using the formula $p=4\gamma \cos\theta/D$ or $f=-[d(F_w/F_d)\times 100]/dD$.

8. The method of claim 4, wherein said porometry test location isolating device is selected from the group consisting of inserts, rings, and sleeves that slidingly engage either an inner or outer surface of said filtration cartridge and direct said test gas through said preselected test location of said cartridge.

9. The method of claim 4, wherein said test location isolating device comprises a ring adapted to slidingly engage an outer surface of a cylindrical filtration cartridge, comprising:

a) a ring member having a groove within an inner surface thereof defining a central gas channel connected to a test gas inlet, said central gas channel arranged to direct flow of said test gas through said ring member to said preselected test location of said cartridge; and b) a pair of gaskets seated within a pair of gasket grooves arranged on each side of said central gas channel, said gaskets defining said test location and confining flow of said pressurized test gas through said test location.

10. The method of claim 4, wherein said test location isolating device comprises a pair of sleeves adapted to slidingly engage an outer surface of a cylindrical filtration cartridge, comprising:

a) a pair of tight fitting rubber sleeves slidingly engaged at each end of a filtration cartridge, said rubber sleeves defining said test location and confining flow of said pressurized test gas through said test location; and b) a test gas inlet located at an end of one of said sleeves, and a sealed end located at an end of the other of said sleeves, with said cartridge being arranged between said sleeves.

11. The method of claim 4, further comprising the step of determining pore structure characteristics at different test locations along the length of said filtration cartridge by moving said test location isolating device to multiple test locations, measuring flow rates and differential pressures at said multiple locations, and converting said measured gas flow rates and differential pressures at said multiple test locations.

12. The method of claim 11, wherein said test location isolating device is moved to said multiple test locations manual or automatically by said flow porometer.

13. The method of claim 4, wherein said test location isolating device comprises an insert adapted to slidingly engage an inner surface of a cylindrical bore of said filtration cartridge, said insert comprising:

a) a tubular member having a test gas inlet at a first end thereof and a sealed second end;

b) a plurality of radial gas channels arranged between said first and second ends of said tubular member for directing flow of said pressurized test gas through said tubular member to said preselected test location of said cartridge; and c) a pair of O-rings seated within a pair of circumferential O-ring grooves arranged between said radial gas channels and said first and second ends of said tubular member, said O-rings defining said test location and confining flow of said pressurized test gas through said test location.

14. The method of claim 13, wherein one of said flexible members attached to said tubular member is a flexible tube member delivering said pressurized test gas to said test gas inlet.

* * * * *